US012727835B2

(12) United States Patent
Jorgensen et al.

(10) Patent No.: US 12,727,835 B2
(45) Date of Patent: Sep. 8, 2026

(54) SYSTEMS AND METHODS FOR STABILIZING A PATIENT LIFT WITH A MEDICAL IMAGING TABLE

(71) Applicant: GE Precision Healthcare LLC, Wauwatosa, WI (US)

(72) Inventors: Anna Jorgensen, Milwaukee, WI (US); Joseph William Burge, Waukesha, WI (US); Ross Christopher Stalter, Waukesha, WI (US); Jiaqi Li, Pewaukee, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 699 days.

(21) Appl. No.: 18/187,600

(22) Filed: Mar. 21, 2023

(65) Prior Publication Data

US 2024/0315650 A1 Sep. 26, 2024

(51) Int. Cl.
*A61B 6/04* (2006.01)
*A61G 7/10* (2006.01)

(52) U.S. Cl.
CPC .......... *A61B 6/0407* (2013.01); *A61G 7/1013* (2013.01); *A61G 7/1046* (2013.01); *A61B 6/04* (2013.01); *A61G 7/104* (2013.01)

(58) Field of Classification Search
CPC ...... A61B 6/0407; A61B 6/04; A61G 7/1013; A61G 7/1017; A61G 7/1019; A61G 7/1046; A61G 7/1044; A61G 7/104; A47C 21/00
USPC ............. 5/601, 600, 84.1, 83.1, 81.1 R, 658, 5/503.1, 507.1; 378/209, 208, 204
See application file for complete search history.

(56) References Cited

U.S. PATENT DOCUMENTS 4,131,802 A * 12/1978 Braden ................ A61B 6/0442 5/81.1 R
4,567,894 A * 2/1986 Bergman ............... A61B 5/055 505/879
4,638,252 A * 1/1987 Bradshaw ........ G01R 33/34046 324/318
4,671,728 A * 6/1987 Clark .................. A61B 6/0487 414/284
6,003,174 A * 12/1999 Kantrowitz .......... A61B 6/0421 5/601
6,199,233 B1 * 3/2001 Kantrowitz .......... A61B 6/0421 5/601
6,557,195 B2 * 5/2003 Dinkler ................ A61B 6/0442 5/601

(Continued)

FOREIGN PATENT DOCUMENTS

EP 2484325 A2 * 8/2012 ........... A61G 7/1046
EP 2594240 B1 11/2014

(Continued)

*Primary Examiner* — Robert G Santos
(74) *Attorney, Agent, or Firm* — McCoy Russell LLP

(57) ABSTRACT

Systems and methods are provided for a patient table. The patient table may include a bed coupled to a base via a midsection and a docking bar coupled to the base. The docking bar may be movable between a first position, where a first longitudinal axis of the docking bar is parallel to a second longitudinal axis of the base, and a second position, where the first longitudinal axis is perpendicular to the second longitudinal axis. The docking bar may include a releasable bottom surface configured to be brought into contact with a base support of a patient lift.

14 Claims, 9 Drawing Sheets

(56) References Cited

U.S. PATENT DOCUMENTS 6,584,630 B1 * 7/2003 Dinkler .................. A61G 13/12 5/643
6,776,527 B1 * 8/2004 Tybinkowski ........... A61B 6/04 378/209
6,973,689 B2 * 12/2005 Lenting ................ A61B 6/0487 5/601
7,293,308 B2 * 11/2007 Everett .................. A61B 5/704 5/601
8,132,276 B2 * 3/2012 Klemm .................. A61G 13/06 5/601
8,336,134 B2 * 12/2012 Jelinek ................. A61G 7/1017 5/83.1
9,248,067 B2 * 2/2016 Sunazuka ............ A61B 6/0407
9,592,024 B2 * 3/2017 Iizuka .................. A61B 6/4411
9,770,378 B2 * 9/2017 Koerth ..................... A61G 7/05
9,789,021 B2 * 10/2017 Sunazuka .............. A61B 6/035
9,861,326 B2 * 1/2018 Koerth ................. A61B 6/0407
11,226,632 B2 * 1/2022 Biber ................... G05D 1/0225
11,925,586 B2 * 3/2024 Lim ....................... A61G 13/06
12,239,468 B2 * 3/2025 Neuber .................. A61B 5/055
12,350,208 B2 * 7/2025 Xue ....................... A61G 7/018
12,453,670 B2 * 10/2025 Lim ....................... A61G 13/06
2002/0174485 A1 11/2002 Bartels
2005/0034237 A1 * 2/2005 Lenting .................. A61B 5/055 5/601
2006/0167356 A1 * 7/2006 Everett ................ A61B 6/0487 600/407
2011/0067179 A1 * 3/2011 Klemm .................. A61G 13/06 5/601
2012/0198613 A1 * 8/2012 Jelinek ................... A61G 7/015 5/86.1
2014/0259411 A1 * 9/2014 Sunazuka ............ A61B 6/4405 5/601
2014/0296692 A1 * 10/2014 Iizuka .................. A61B 6/0487 600/407
2014/0303477 A1 * 10/2014 Sunazuka ............ A61B 6/0407 600/407
2014/0335734 A1 * 11/2014 Koerth ................... A61B 5/704 439/626
2015/0272518 A1 * 10/2015 Koerth ................... A61B 5/704 5/601
2018/0329422 A1 * 11/2018 Biber ................... G05D 1/0225
2022/0047218 A1 * 2/2022 Neuber .................. A61B 5/704
2022/0265496 A1 * 8/2022 Xue ....................... A61G 7/018
2023/0301862 A1 * 9/2023 Lim ....................... A61G 13/06
2024/0164969 A1 * 5/2024 Lim ....................... A61G 13/06
2024/0315650 A1 * 9/2024 Jorgensen ............ A61G 7/1013
2025/0248875 A1 * 8/2025 Liu .......................... A61B 6/04

FOREIGN PATENT DOCUMENTS

EP 2851051 A1 * 3/2015 ............. A61G 7/015
EP 2851051 B1 * 7/2016 ............. A61G 7/015
WO WO-03041577 A1 * 5/2003 ........... A61B 6/0487
WO WO-2004047639 A1 * 6/2004 ............. A61B 5/055

* cited by examiner

SYSTEMS AND METHODS FOR STABILIZING A PATIENT LIFT WITH A MEDICAL IMAGING TABLE

TECHNICAL FIELD

The present description relates generally to a detachable MR table. More specifically, the present disclosure relates to a detachable MR table that facilitates stabilization of a patient lift.

BACKGROUND

Magnetic resonance imaging (MRI) scanners may be configured to generate medical images of anatomy and physiological processes through the use of magnetic fields, magnetic field gradients, and radio waves. During an MRI scan, a patient may be positioned on an MR table that is constructed of non-ferrous materials. Such a table may be able to move in and out of the MRI scanner through an MRI bore, allowing patients to get on and off the table outside of the scanner. Some patients, such as those that require a wheelchair for mobility, may require assistance onto an MR table. As such, a patient lift may facilitate the transfer of some patients onto an MR table. Transferring a patient via a patient lift often occurs outside of the room that contains the MRI scanner due to the metallic nature of some patient lifts. Therefore, some MR tables may detach from the MRI scanner for patient transfer and reattach to the MRI scanner for imaging.

BRIEF DESCRIPTION

In one example, the issues described above may be addressed by a patient table (e.g., an MR table) that includes a bed coupled to a base via a midsection and a docking bar coupled to the base. The docking bar may be movable between a first position, where a first longitudinal axis of the docking bar is parallel to a second longitudinal axis of the base, and a second position, where the first longitudinal axis is perpendicular to the second longitudinal axis. The docking bar may include a releasable bottom surface configured to be brought into contact with a base support of a patient lift. In this way, the docking bar may stabilize the patient lift, preventing the patient lift from tipping over as the patient is repositioned and the patient lift may be able to more easily position a patient directly over the patient table during patient transfer. Additionally, the docking bar may be compatible with the existing internal geometry of detachable MR tables on the market, and as such can be installed onto tables that are already in use with no or minor modification of the non-structural components of each table.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
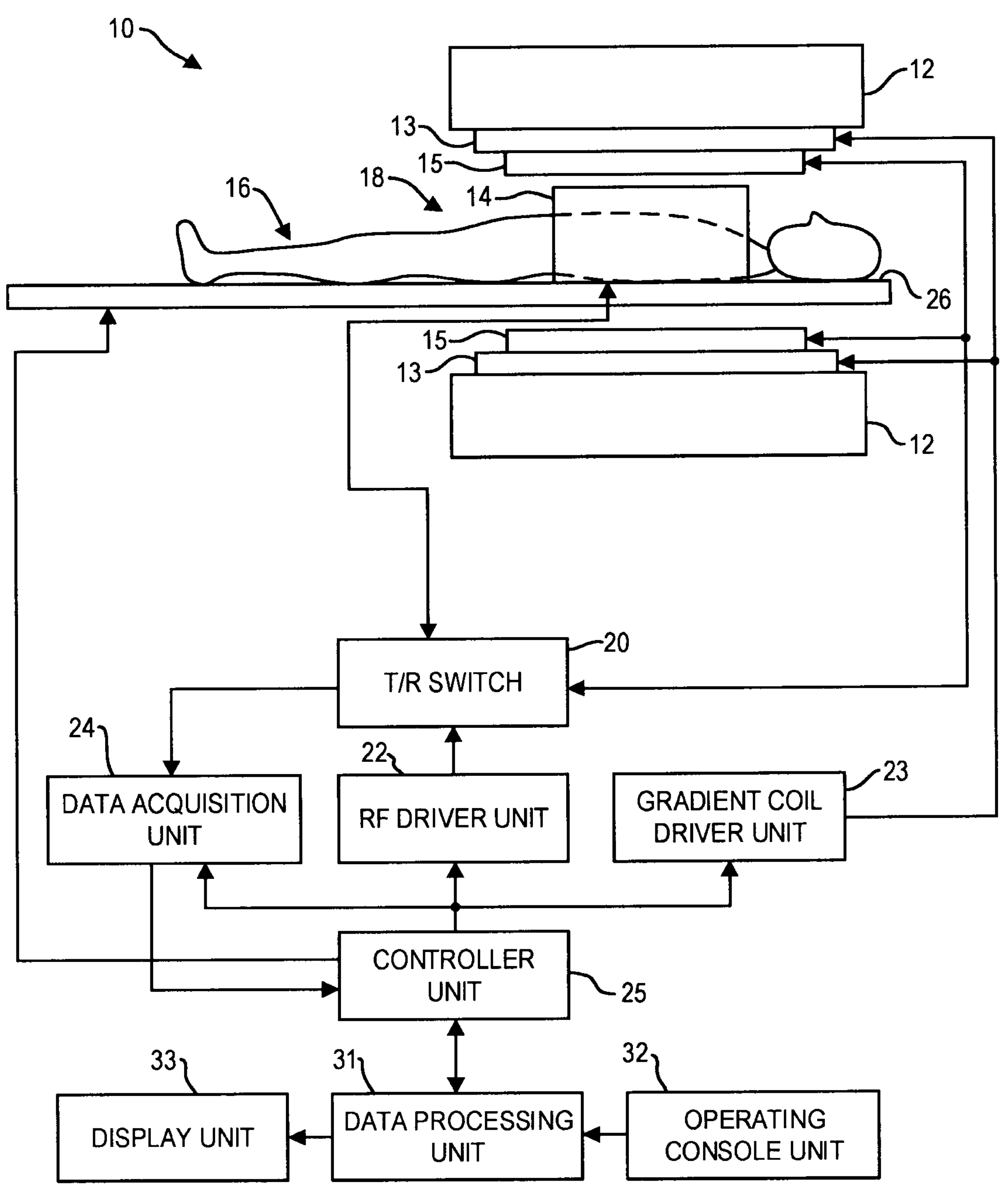
FIG. 1 is a block diagram of an MRI system according to an embodiment of the disclosure.

The following description relates to a patient table. The patient table may be configured to stabilize a patient lift to facilitate transfer of a patient to the patient table. For example, the patient table may include a bed coupled to a base via a midsection and a docking bar coupled to the base. The docking bar may be movable between a first position, where a first longitudinal axis of the docking bar is parallel to a second longitudinal axis of the base, and a second position, where the first longitudinal axis is perpendicular to the second longitudinal axis. The docking bar may include a releasable bottom surface configured to be brought into contact with one or more base supports of a patient lift. In another example, additionally or alternatively, the patient table may include a first scissor lift mechanism and a second scissor lift mechanism. Each of the first scissor lift mechanism and the second scissor lift mechanism may be housed in the midsection of the patient table and coupled to the base and to the bed of the patient table and configured to raise the bed from a lowered position to a raised position. In at least the raised position, a first clearance gap and a second clearance gap may be exposed within the base and between the first and second scissor lift mechanisms.

As scan times keep getting shorter, patient transfer and set up time become more important for, and a larger fraction of, the total Takt time (e.g., time between patient start times). For some patients that use a wheelchair, it can be very difficult to transfer them to a magnetic resonance (MR) table without a patient lift. Some medical/imaging facilities may utilize a ceiling-mounted patient lift, but ceiling-mounted patients lifts are expensive and demand space and/or structural features that may not be readily available at all medical/imaging facilities. As such, many medical/imaging facilities only utilize mobile patient lifts, which are ferrous and cannot be used for patient transfer inside of the scan room. Because the feet of the patient lift do not fit most detachable MR tables, operators may improvise workarounds to stabilize the patient lift and facilitate patient transfer to the MR table. For example, other attempts to address the lack of compatibility between patient lifts and detachable MR tables include positioning the lift at the end of the detachable MR table instead of at the side, or using an alternative patient transfer mechanism instead of a patient lift.

However, placing a heavy patient on a detachable MR table from the end instead of the side may cause a weight imbalance, which may be hazardous for both the patient and for the technologist. Additionally, it may be much easier to transfer a patient from a wheelchair to a patient lift than to transfer a patient from a wheelchair to a patient gurney or other type of transfer table. Further, a patient gurney may only be useful for transferring patients onto the table of a medical imaging system, while a patient lift that is similar to common patient lift products available on the market may serve additional purposes and therefore may be more cost effective. Thus, it may be advantageous to utilize patient lifts rather than gurneys or other types of transfer tables.

Patient tables utilized for medical imaging, such as MR tables, may be configured to precisely position a patient within a bore or gantry of the imaging system and may be configured to adjust a height of a bed of the patient table from a lowest possible height to a highest possible height (and heights there between), where the lowest possible height of the bed is as low as possible to facilitate easy transfer of smaller patients to the table and the highest possible height is based on the height of the bore or gantry of the imaging system. Thus, patient tables for medical imaging may be constrained between the lowest and highest possible heights and may include internal components to facilitate adjustment of the bed height, facilitate lateral movement of the bed into the bore or gantry, facilitate imaging (e.g., embedded RF coils), facilitate brakes and steering of the table, and the like.

Thus, embodiments for MR tables are disclosed herein that are configured to stabilize patient lifts while also maintaining demanded bed height constraints and functionality of the patient table for medical imaging. The MR tables disclosed herein may be utilized with an MRI apparatus, such as the MRI apparatus shown in FIG. 1. The MR table includes, in one embodiment, a table bed coupled to a base via a midsection and a docking bar coupled to the base, as shown in FIG. 2. The docking bar may be movable between a first position, where a first longitudinal axis of the docking bar is parallel to a second longitudinal axis of the base, and a second position, shown in FIG. 3, where the first longitudinal axis is perpendicular to the second longitudinal axis. As illustrated in FIG. 4, the docking bar may include a pedal that controls a releasable bottom surface, where the bottom surface is configured to be brought into contact with one or more base supports of a patient lift. FIG. 5 shows a method for transferring a patient from a patient lift to the MR table. The MR table illustrated in FIGS. 2-4 may thereby stabilize a patient lift with a docking bar that swings outward from a side of the table, where the docking bar is accommodated within existing space along the side of the MR table and without demanding a change in height of or position of a structural member of the MR table.

Figure 6:
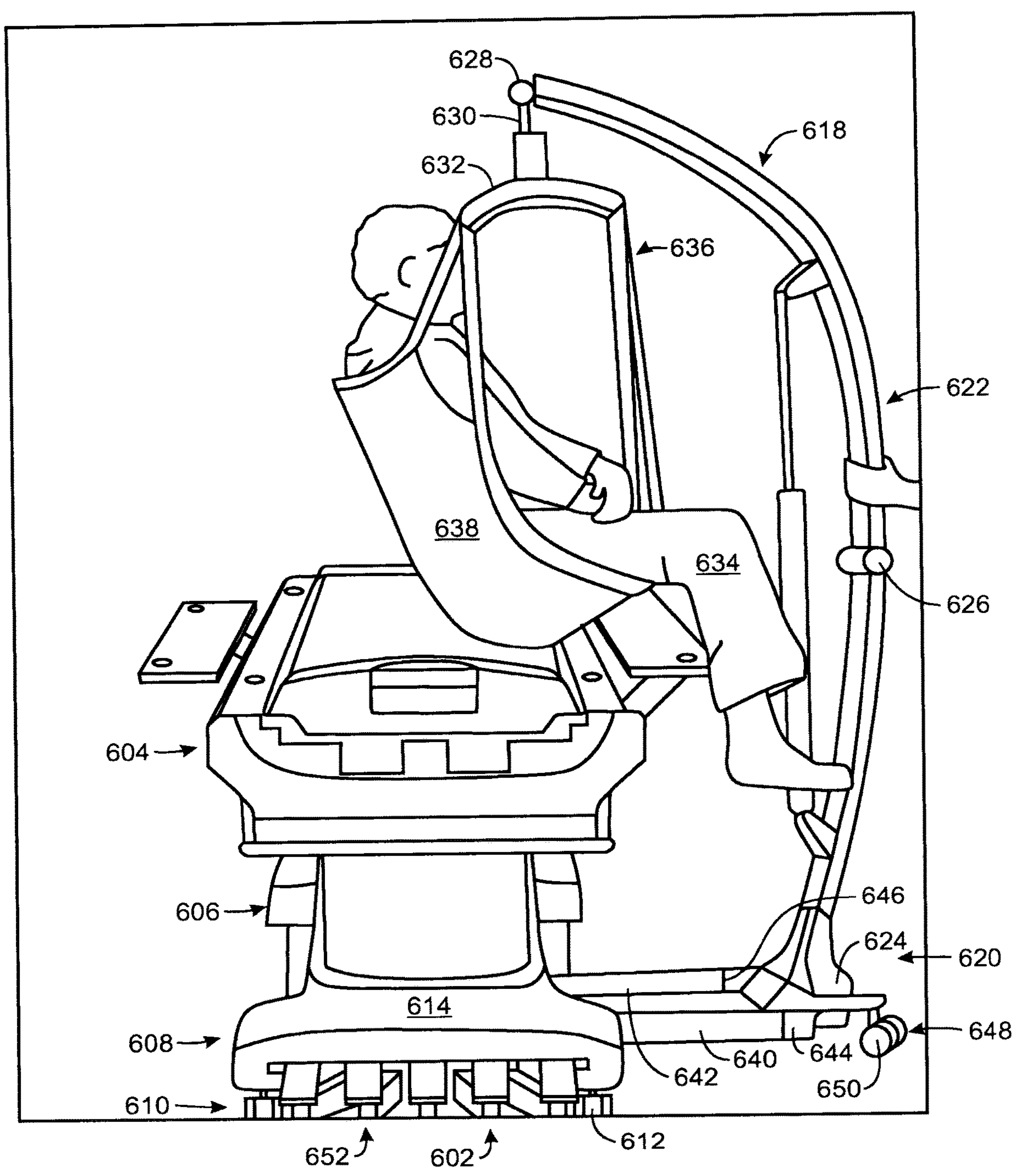
FIG. 6 shows a front perspective view of a second embodiment of a detachable MR table configured to facilitate stabilization of a patient lift.
Figure 7:
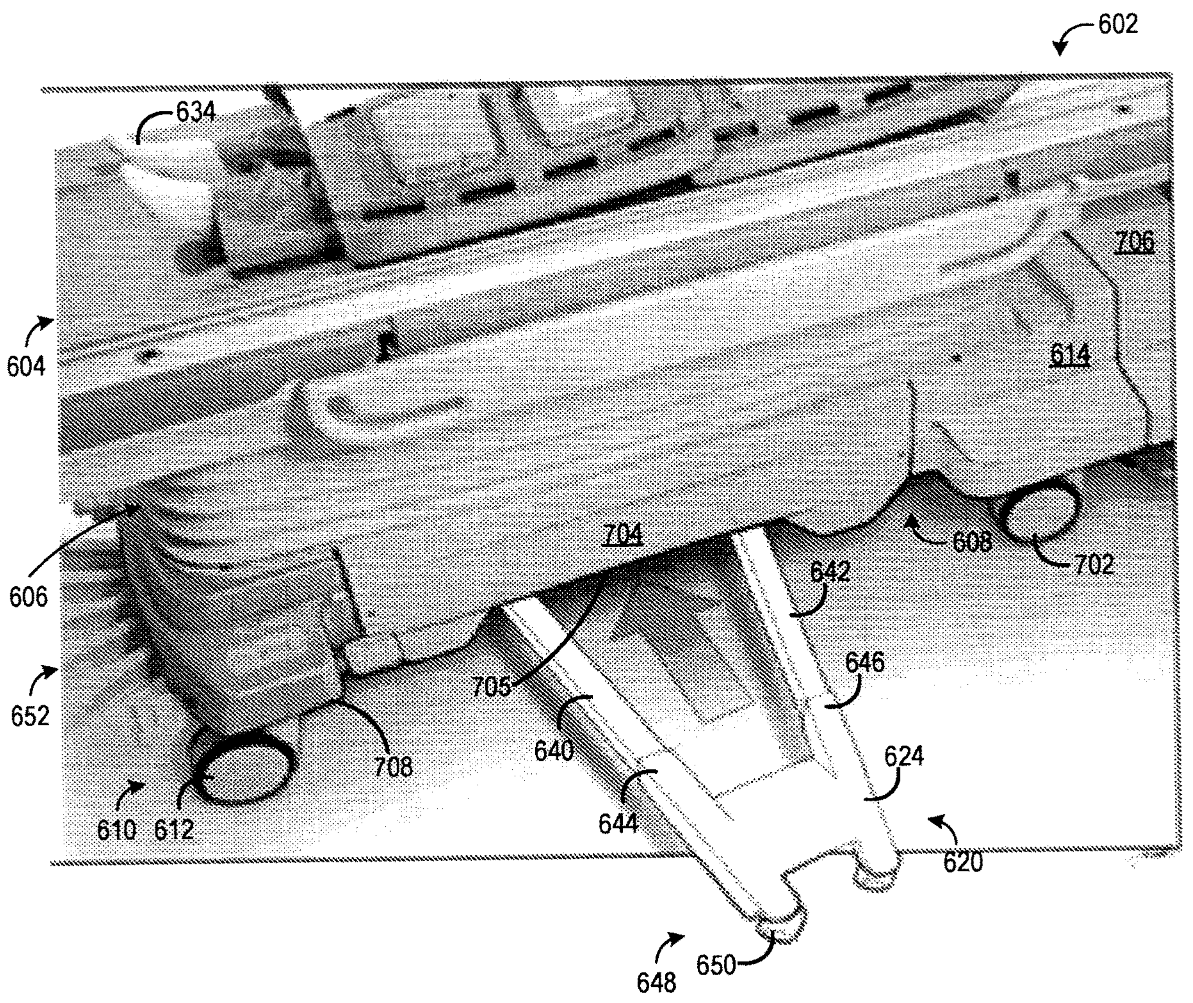
FIG. 7 shows a side perspective view of the detachable MR table of FIG. 6.
Figure 8A:
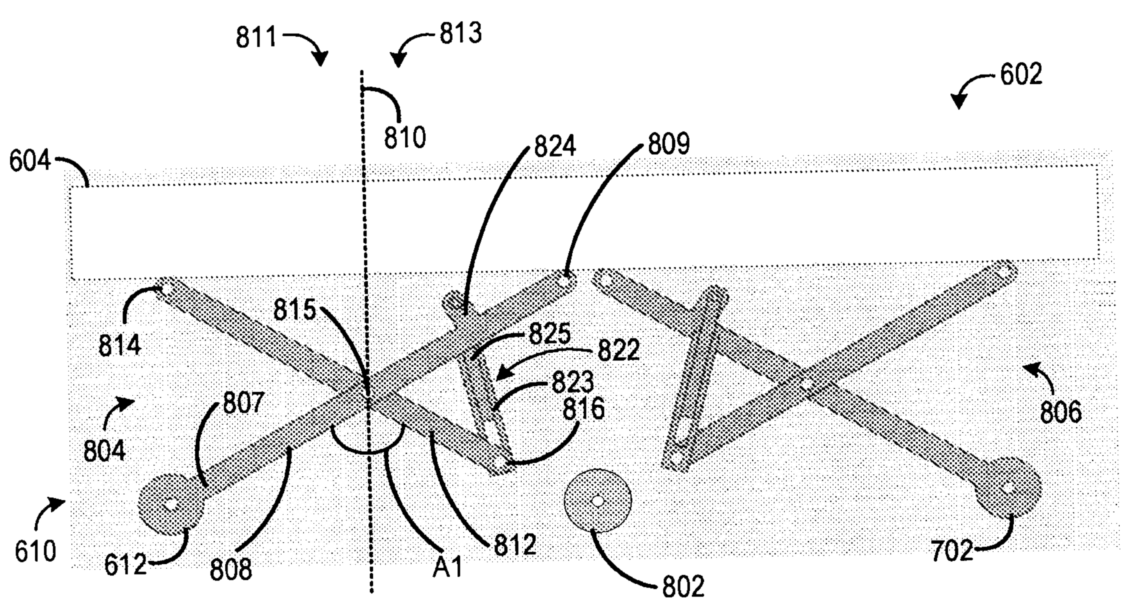
FIG. 8A shows a side view of the detachable MR table of FIG. 6 in a lowered position.
Figure 8B:
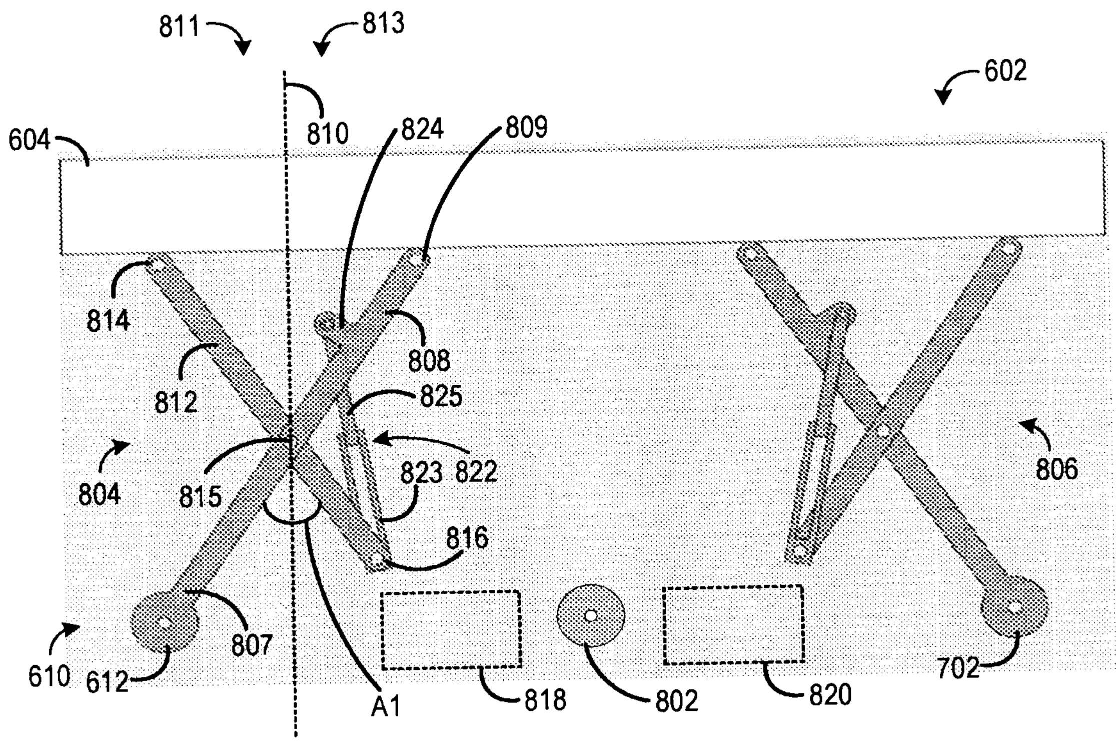
FIG. 8B shows a side view of the detachable MR table of FIG. 6 in a raised position.
Figure 9:
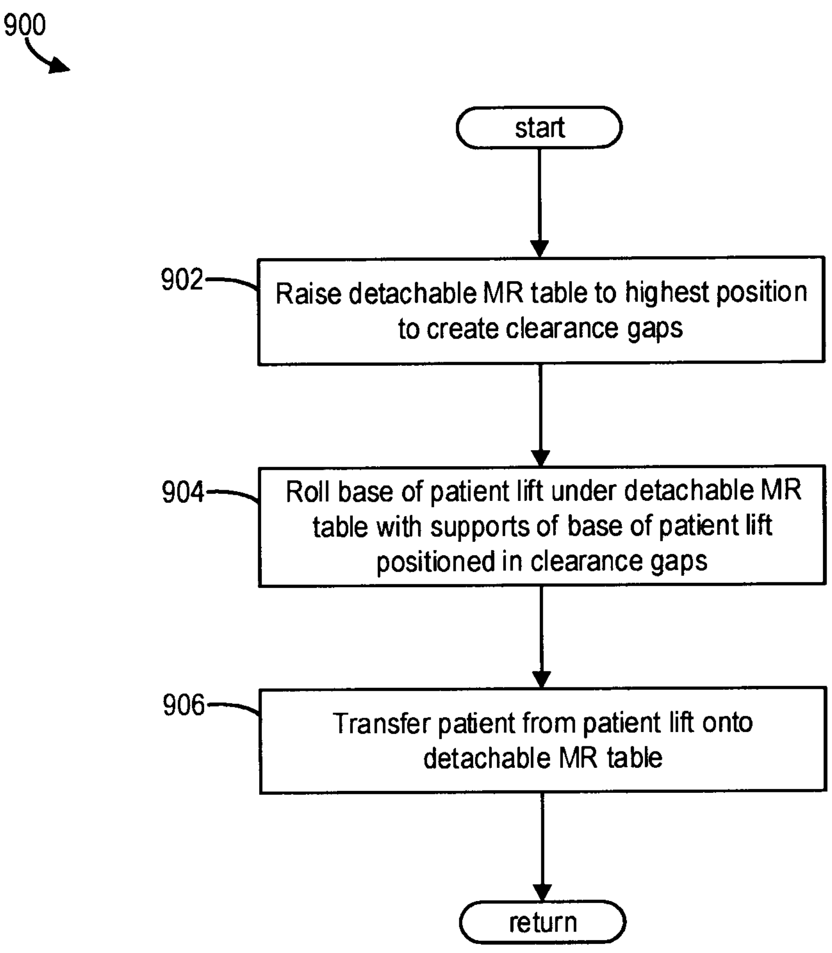
FIG. 9 is a flowchart illustrating a method for transferring a patient from a patient lift to the detachable MR table of FIG. 6.

The MR table includes, in another embodiment, a table bed coupled to a base via a midsection, where the base may accommodate the base supports of a patient lift as shown in FIGS. 6 and 7. As illustrated in FIGS. 8A and 8B, the MR table may accommodate the base supports of the patient lift in clearance gaps that are created by two scissor lift mechanisms. FIG. 9 shows a method for transferring a patient from a patient lift to the MR table. The MR table illustrated in FIGS. 6-8B may thereby stabilize a patient lift via clearance gaps formed between two separate scissor lift mechanisms, which may allow the base supports of patient lifts to be moved under the bottom of the MR table while still allowing the lowest possible bed height to be achieved (e.g., without simply raising the height of the frame of the patient table).

Figure 2:
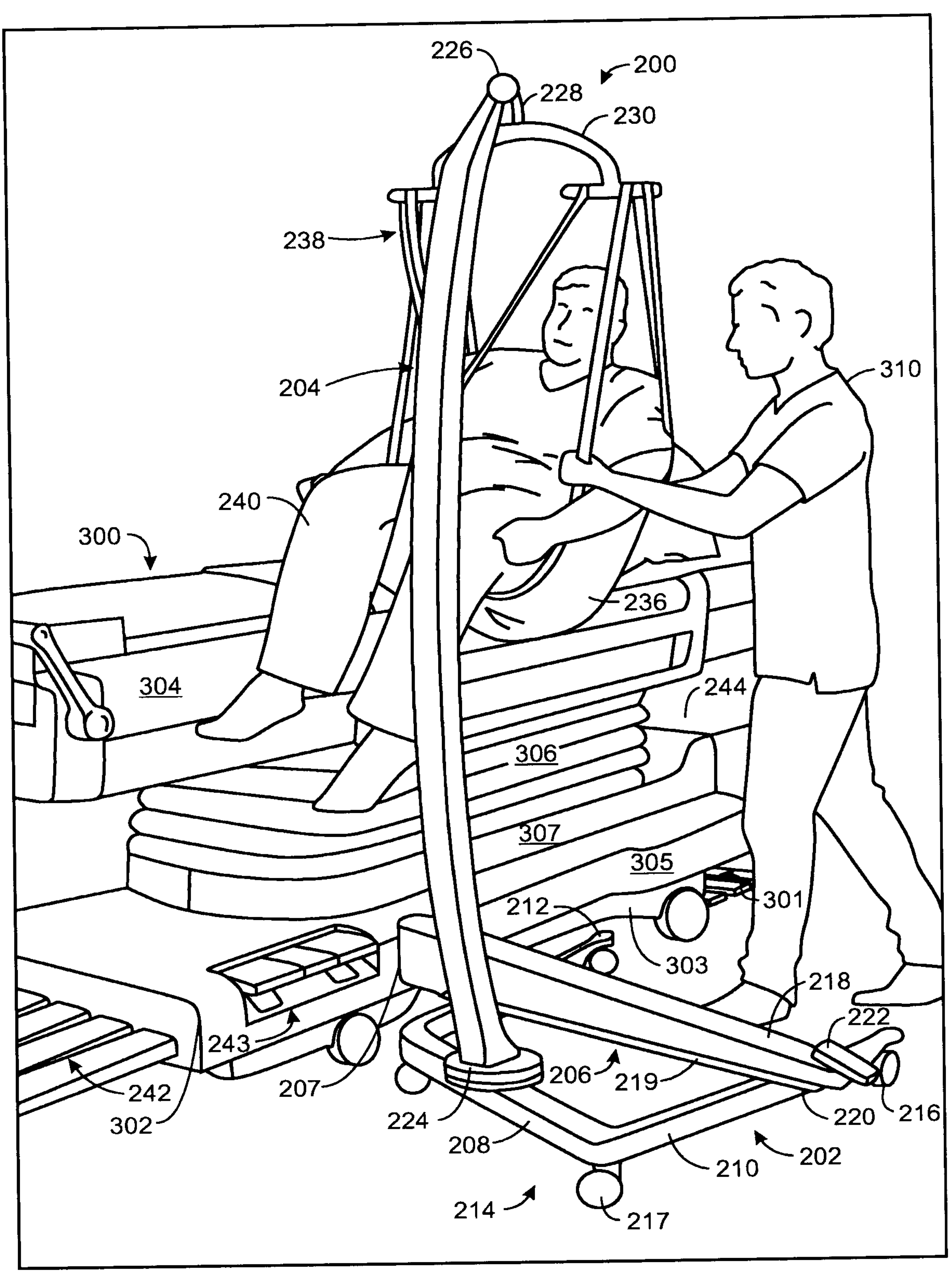
FIG. 2 shows a side perspective view of a first embodiment of a detachable MR table configured to facilitate stabilization of a patient lift.

FIG. 1 illustrates an MRI apparatus 10 that includes a magnetostatic field magnet unit 12, a gradient coil unit 13, an RF coil unit 14, an RF body coil unit 15 (e.g., volume coil unit), a transmit/receive (T/R) switch 20, an RF driver unit 22, a gradient coil driver unit 23, a data acquisition unit 24, a controller unit 25, a patient bed or table 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface of the RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF body coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF body coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF body coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

Figure 3:
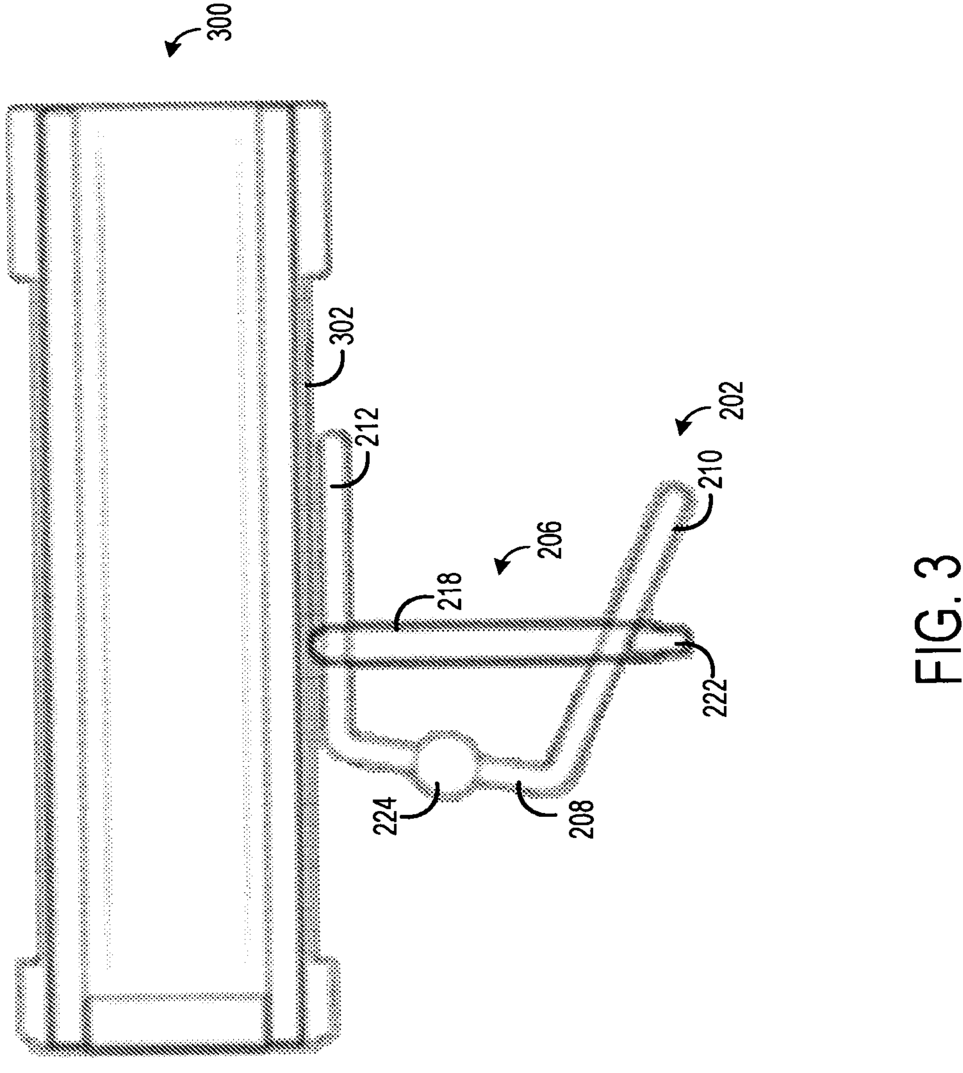
FIG. 3 shows a top view of the detachable MR table of FIG. 2.
Figure 4:
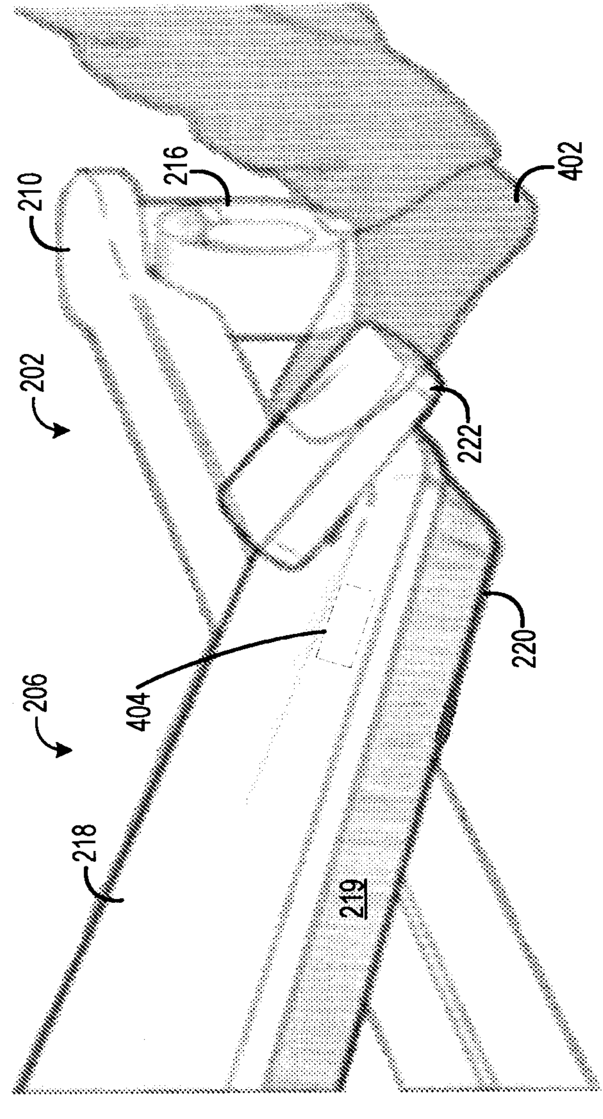
FIG. 4 shows a zoomed-in view of a docking bar and a pedal of the detachable MR table of FIG. 2.
Figure 5:
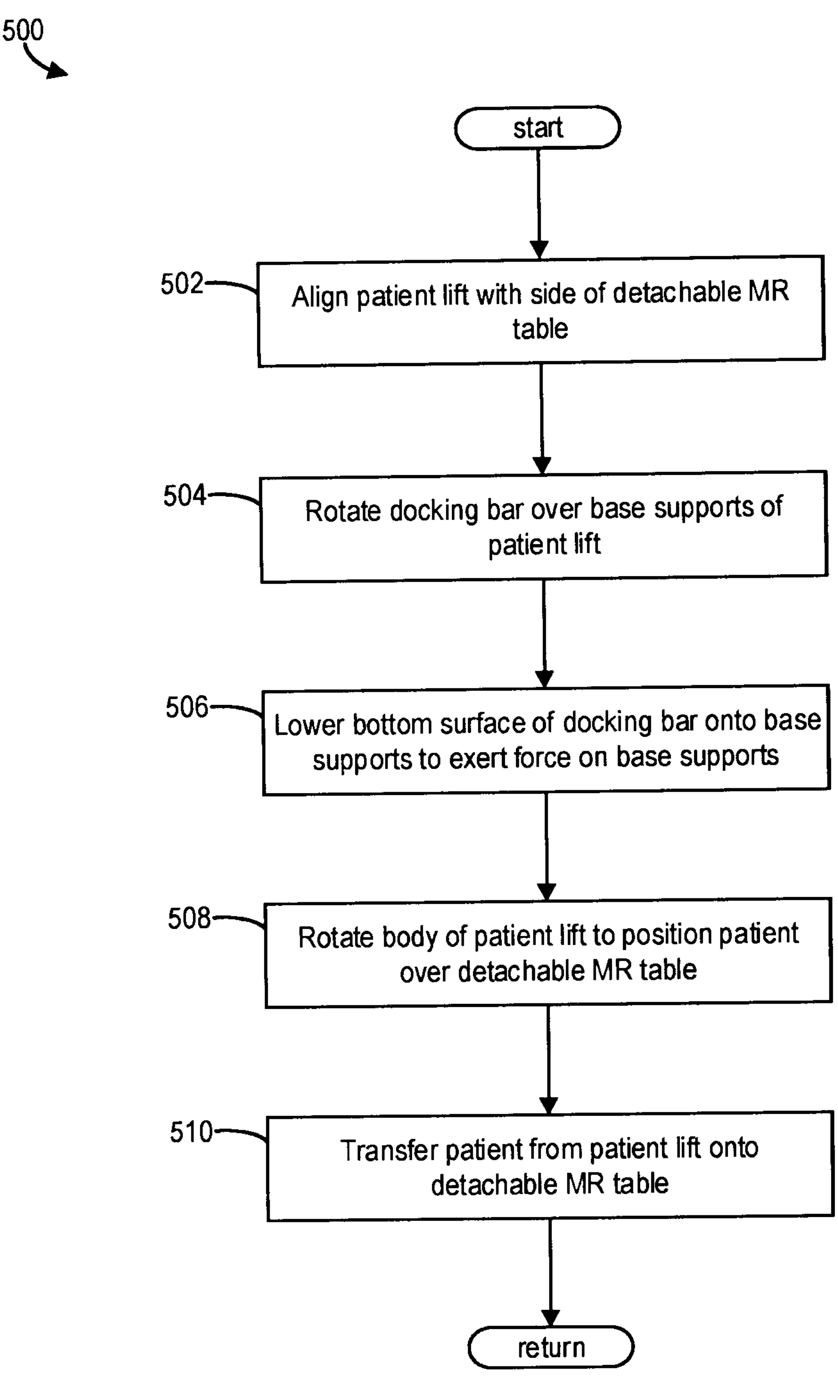
FIG. 5 is a flowchart illustrating a method for transferring a patient from a patient lift to the detachable MR table of FIG. 2.

FIGS. 2-4 show a first embodiment of a detachable MR table that facilitates stabilization of a patient lift, and are described collectively. FIG. 2 illustrates an MR table 300. The MR table 300 may be configured for use in a medical imaging scanner, such as the MRI apparatus 10 of FIG. 1. Further, at least a portion of the MR table 300 may be configured to be positioned within a bore of the medical imaging scanner. As such, at least a portion of the MR table 300 may be of a suitable shape and size to pass through a bore of a medical imaging scanner, and fit inside of the medical imaging scanner during imaging. While the MR table 300 may be configured for use with a magnetic resonance imaging scanner, the MR table 300 may be configured for another suitable medical imaging scanner (e.g., x-ray, CT, PET, SPECT, etc.) without departing from the scope of this disclosure.

In the example illustrated in FIG. 2, one or more surfaces of the MR table 300 may be designed to temporarily couple to an MRI scanner. In this way, the MR table 300 may be attached to the MRI scanner for stability during medical imaging, and may be detached and moved away from the MRI scanner for patient loading. While the MR table 300 is detached from the MRI scanner, the MR table 300 is more susceptible to tipping over due to weight imbalance during patient loading and unloading. Additionally, the reduced stability of the MR table 300 while it is detached from the MRI scanner may increase the difficulty of stabilizing a patient lift while transferring a patient onto the MR table 300.

The MR table 300 may include a table bed 304, a table midsection 306, and a table base 301. The table midsection 306 may be intermediate the table bed 304 and the table base 301, with the table bed 304 being above the table midsection 306 and the table base 301 being below the table midsection 306, relative to the direction of gravity when the MR table 300 is positioned on flat ground. The table bed 304 may couple to the table midsection 306, and the table midsection 306 may couple to the table base 301.

The table bed 304 of the MR table 300 may be configured to accommodate a patient during medical imaging. As such, the top surface of the table bed 304 may be flat, relative to the ground. Additionally, at least a portion of the top surface of the table bed 304 may be constructed of a compressible material (e.g., foam, cotton, polyester, etc.). In some examples, the table bed 304 may include embedded RF coils for receiving signals from an MRI scanner. The table bed 304 may have a length in a range of 180 to 220 cm and a width in a range of 60 to 92 cm. At least a portion of the table bed 304 may be moved laterally, relative to the table midsection 306 and the table base 301. The lateral movement of the table bed 304 may be used to position at least a portion of the table bed 304 and an accommodated patient into a medical imaging scanner (e.g., an MRI scanner). In some examples, at least one side of the table bed 304 may include rails or guards that may be used to assist a patient on or off the MR table 300 and/or may provide support for a patient when the MR table 300 is being moved.

The table midsection 306 may include structural elements that at least in part support the table bed 304 against the force of gravity. Additionally, the table midsection 306 may include at least a portion of a lifting mechanism (e.g., hydraulic piston, mechanical piston, scissor lift, etc.) which may allow the table bed 304 to change height relative to the table base 301. As such, the table bed 304 may be lowered for patient transfer onto the MR table 300 and the table bed 304 may be raised for medical imaging, for example. In some examples, the table bed 304 may have a minimum height of 50 cm and a maximum height of 95 cm.

In some examples, the table midsection 306 may have a shorter length and a narrower width relative to the length and width of the table bed 304, respectively. As such, the table midsection 306 may have a length in a range of 120-185 cm and a width in a range of 40-72 cm. The table midsection 306 having a shorter length and/or narrower width than the table bed 304 may contribute to the instability of the MR table 300 when moving a patient onto the MR table 300 from a patient lift, particularly when the patient is moved onto the MR table 300 at one of the ends of the MR table (e.g., a front end or back end).

The table base 301 of the MR table 300 may provide structural support for the table midsection 306 and the table bed 304 of the MR table 300. In some examples, the table base 301 may be longer and wider than the table midsection 306. As such, the table base may have a length in a range of 180-220 cm and a width in a range of 60-92 cm. Additionally, the table base 301 may have a height in a range of 25-45 cm, from the ground to the highest point of the table base 301.

The table base 301 may include a lower base 305 and an upper base 307, where the lower base 305 is positioned below the upper base 307, as shown in FIG. 2. In some examples, the lower base 305 may be wider and longer than the upper base 307. The table base 301 may include a frame 303 with a plurality of wheels that allow the MR table 300 to be moved translationally across a floor. In some examples, the frame 303 may have four wheels or six wheels. The frame 303 may be positioned under the lower base 305, relative to the direction of gravity. The table base 301 may include a plurality of pedals 242 located on the front (e.g., the side most distal to a medical imaging scanner during imaging) of the table base 301. In some examples, the plurality of pedals 242 may actuate the raising and/or lowering of the table bed 304 via a lifting mechanism in the table midsection 306 and the detachment and/or reattachment of the MR table 300 from a medical imaging scanner (e.g., an MRI scanner). The table base 301 may include a plurality of pedals 243 located on the side of the table base 301. In some examples, the plurality of pedals 243 may actuate the engagement and/or disengagement of a brake (e.g., to prevent translational movement of the MR table 300) and the engagement and/or disengagement of a steering lock. Additionally, the table base 301 may include a dock 244 that allows the MR table 300 to attach to a medical imaging scanner (e.g., an MRI scanner). The dock 244 may be located on the back of the table base 301, opposite to the plurality of pedals 242. The table base 301 may include a housing 302 where the inner volume of the housing 302 may envelope some or all of the table base 301.

The MR table 300 further includes a docking bar 206 coupled to one longitudinal side of the frame 303 of the table base 301. The housing 302 may include an opening through which the docking bar 206 may protrude. The docking bar 206 may include a body 218, a lift stabilizer 219 at least partially housed within the body 218, and a pedal 222. Further, the docking bar 206 may be comprised of a non-ferrous material. The body 218 of the docking bar 206 may include a connecting end 207. The connecting end 207 of the docking bar 206 may be mounted on the table base 301 via a hinge mechanism (e.g., flush hinge, flag hinge, case hinge, etc.), or another suitable hinge-like mechanism. As such, the connecting end 207 of the docking bar 206 may act as a pivot axis that the docking bar 206 can rotate around. In some examples, the docking bar 206 may rotate around the connecting end 207 from a first position that is approximately parallel to the longitudinal axis of the MR table 300, to a second position that is approximately perpendicular to the MR table 300, as shown in FIG. 3.

The connecting end 207 of the docking bar 206 may couple to the frame 303 of the table base 301 at a position that is within the lower base 305 of the table base 301. In some examples, the top-most point of the connecting end 207 may couple to the frame 303 at a height that is level with the top-most point of the lower base 305, relative to the y-axis. Additionally, the connecting end 207 may couple to the table base 301 at a position that is 60-80% of the way towards the front (e.g., the side of the table base 301 that includes the plurality of pedals 242) along one longitudinal side of the table base 301.

The body 218 of the docking bar 206 may have a width in a range of 5-15 cm. The body 218 of the docking bar 206 may have a height in a range of 10-20 cm at the connecting end 207 and a height in a range of 5-15 cm at the end of the docking bar 206 that is most distal to the connecting end 207. When in the raised position, the lift stabilizer 219 of the docking bar 206 may extend in a range of 2-20 cm downwards from a bottom edge of the body 218 of the docking bar 206. The top surface of the body 218 of the docking bar 206 may gradually decline from the connecting end 207 to the distal end. Additionally, the body 218 of the docking bar 206 may have a length in a range of approximately 100-150 cm from the connecting end 207 to the end of the docking bar 206 that is most distal to the connecting end 207.

The lift stabilizer 219 may include an internal body (e.g., a frame) having a releasable bottom surface 220, where the releasable bottom surface 220 is a bottom-most surface of the lift stabilizer 219. The releasable bottom surface 220 of the docking bar may be substantially flat and may be positioned outside of the body 218 of the docking bar 206 in some examples. Further, the releasable bottom surface 220 may be constructed of a material with a high coefficient of friction. In some examples, the releasable bottom surface 220 may be a piece of rubber or a layer of plastic along a bottom surface of the lift stabilizer 219. In some examples, the lift stabilizer 219 may include side walls coupled to the releasable bottom surface 220 and at least partially enclosing the internal body of the lift stabilizer 219.

The releasable bottom surface 220 of the lift stabilizer 219 may be releasable, and may therefore be configured to move downward relative to the body 218 by a distance in a range of 5-15 cm. Thus, when the releasable bottom surface 220 is lowered from the lift stabilizer 219, the clearance between the docking bar 206 and the ground may be reduced. As such, the releasable bottom surface 220 of the lift stabilizer 219 may come into face sharing contact with an object under the docking bar 206, such as a patient lift. In some examples, the clearance between the releasable bottom surface 220 of the lift stabilizer 219 and the ground may be in a range of 5-50 cm when the lift stabilizer 219 is not actuated and a range of 3-30 cm when the lift stabilizer 219 is fully actuated. For example, the releasable bottom surface 220 may be positioned with a clearance of 10-30 cm from the ground when the lift stabilizer 219 is not actuated (e.g., not lowered) and may be lowered to have a clearance of 5-15 cm from the ground when the lift stabilizer 219 is actuated. It is to be appreciated that the clearance between the releasable bottom surface 220 and the ground, in the retracted/non-lowered and in the deployed/lowered positions, may be based on the specific table dimensions (e.g., the height of the base of the table) and the height of a base of a patient lift to be stabilized by the docking bar, as will be explained in more detail below. In some examples, the releasable bottom surface 220 of the lift stabilizer 219 may exert a predetermined amount of pressure (e.g., force) onto the top of a patient lift. As such, the docking bar 206 may be used to stabilize a patient lift, such as a patient lift 200 of FIG. 2, by exerting a constant downward force onto the patient lift.

The pedal 222 may couple to the end of the body 218 of the docking bar 206 that is most distal the connecting end 207. As illustrated in FIG. 4, a foot of an operator 402 may step on the pedal 222 to actuate the lowering and/or lifting of the releasable bottom surface 220, relative to the ground. The pedal 222 may activate a first actuator 404 that is positioned within the body 218 of the docking bar 206. In some examples, the first actuator 404 may be a hydraulic system, a mechanical piston, or a spring release.

In some examples, rotating a top surface of the pedal 222 toward the operator 402 (e.g., rotating the end of the pedal 222 that is most distal the connecting end 207 toward the ground) may cause the first actuator 404 to move the releasable bottom surface 220 (e.g., via the internal body/frame of the lift stabilizer 219) from a retracted position toward the ground (e.g., away from the body 218). Once lowered into a deployed position, the releasable bottom surface 220 may be held in place by a hydraulic force, a spring, a piston, or another suitable locking mechanism of the first actuator 404. Additionally, in some examples, rotating a top surface of the pedal 222 away from the operator 402 (e.g., rotating the end of the pedal 222 that is most distal the connecting end 207 away from the ground) may cause the first actuator 404 to raise (e.g., retract) the releasable bottom surface 220 away from the ground (e.g., back toward the body 218). In other examples, a switch, a pedal, or another suitable release mechanism may cause the first actuator 404 to raise the lift stabilizer 219 back toward and/or into the body 218 of the docking bar 206.

The patient lift 200 may include a base 202 and a body 204, where the base 202 is coupled to the body 204 via a swiveling joint 224. The base 202 of the patient lift 200 may comprise a first support 210, a second support 212, and a connecting section 208, where the connecting section 208 is intermediate the first support 210 and the second support 212. As shown in FIG. 3, one longitudinal end of the first support 210 may be coupled to one longitudinal end of the connecting section 208 at an angle of approximately 100 degrees. Similarly, one longitudinal end of the second support 212 may be coupled to the other longitudinal end of the connecting section 208 at an angle of approximately 100 degrees. Additionally, the base 202 may include a plurality of wheels 214, such as a first wheel 216 and a second wheel 217, that may allow the patient lift 200 to move translationally along the floor.

The body 204 of the patient lift 200 may include a pulley 226, a line 228, and a hanger 230. The pulley 226 may be positioned at the highest point of the body 204, relative to the direction of gravity, and the line 228 may be wrapped around the pulley 226. The line 228 may be a rope, cable, chain, or other material suitable for use with a pulley. The hanger 230 may be attached to one end of the line 228 so that the line 228 may raise or lower the hanger 230 as the line moves around the pulley 226. The hanger 230 may support a sling 236 via a plurality of sling straps 238. As such, a patient 240 may be supported by the patient lift 200 while sitting in the sling 236.

While supporting the patient 240, the patient lift 200 may be positioned such that one support (e.g., the second support 212) of the base 202 is within a certain distance (e.g., within 10-20 cm) of one side of the table base 301 of the MR table 300, as shown is FIG. 2. An operator 310 may use the pedal 222 to lower the docking bar 206 onto the base 202 of the patient lift 200. As such, the releasable bottom surface 220 of the docking bar 206 may exert a downward force onto the first support 210 and the second support 212 of the base 202. In this way, the docking bar 206 may prevent translational movement of the patient lift 200 along the ground. Additionally, the docking bar 206 may prevent any of the wheels of the plurality of wheels 214 from lifting off of the ground (e.g., the docking bar 206 may keep the first support 210, the second support 212, and the connecting section 208 in a plane that is parallel to the plane of the ground). As such, the swiveling joint 224 may be rotated, and at least a portion of the sling 236 and the patient 240 may be positioned over at least a portion of the MR table 300 without the patient lift 200 tipping over.

FIG. 5 is a flowchart illustrating a method 500 for transferring a patient from a patient lift to a detachable MR table. The patient lift may be a non-limiting example of the patient lift 200 of FIG. 2. Similarly, the detachable MR table may be a non-limiting example of the MR table 300 of FIG. 2. Method 500 may be executed by an operator, such as the operator 310 of FIG. 2.

At 502, method 500 may include aligning the patient lift with one side of the detachable MR table. The patient lift may be aligned through the use of wheels, such as the plurality of wheels 214 of FIG. 2. One support of a base of the patient lift, such as the second support 212 of FIGS. 2 and 3, may be oriented with its longitudinal axis approximately parallel to a side of the detachable MR table on which a docking bar is mounted. Additionally, the support may be positioned within a certain distance (e.g., within 10-20 cm) of a base of the detachable MR table.

At 504, method 500 may include rotating a docking bar of the MR table over the supports of the base of the patient lift. The docking bar may be the docking bar 206 of FIG. 2 in some examples, and may couple to one side of the base of the detachable MR table. The docking bar may be rotated from a first position, where the longitudinal axis of the docking bar is approximately parallel to the side/longitudinal axis of the detachable MR table, to a second position, where the longitudinal axis of the docking bar is approximately perpendicular to the side/longitudinal axis of the detachable MR table, as shown in FIG. 3. A connecting end of the docking bar, such as connecting end 207 of FIG. 2, may couple the docking bar to the base of the detachable MR table and may act as a pivot axis for the docking bar to rotate around.

When the docking bar is in the second portion (e.g., the longitudinal axis of the docking bar is approximately perpendicular to the side of the detachable MR table), the docking bar may be positioned so that it crosses over the supports of the base of the patient lift (e.g., the first support 210 and the second support 212 of FIGS. 2 and 3). The docking bar may cross over the support that was aligned to have its longitudinal axis approximately parallel to the side of the detachable MR table that includes the docking bar, as well as another support of the patient lift. The docking bar may be positioned at a height that is higher than a top surface of the base of the patient lift, such that the docking bar is not making contact with the base of the patient lift.

At 506, method 500 may include lowering the bottom surface of the docking bar onto the base supports so that the docking bar exerts a force on the base supports. To lower the bottom surface, a pedal of the docking bar may be depressed to activate an actuator and release the bottom surface and enable the released bottom surface to move downward (toward the ground). The pedal may be pedal 222 of FIGS. 2-4, and may be angled by a foot of an operator in order to actuate a vertical movement of the docking bar. When the end of the pedal closest to the operator is angled downward, the bottom surface of the docking bar may be lowered toward the base of the patient lift. However, in other examples, the bottom surface may be lowered via an alternative mechanism, such as a mechanical button, a lever, an electronic mechanism, or another suitable actuator.

Lowering the bottom surface of the docking bar may include releasing/lowering a releasable bottom surface of the docking bar so that the releasable bottom surface contacts a top surface of both of the supports of the base of the patient lift, and in doing so may exert a downward force on the base of the patient lift. The pedal may remain in an angled position until the operator actuates the pedal back to its original position. While the pedal is in an angled position, the bottom surface of the docking bar may not be raised away from the supports of the base of the patient lift. In this way, the docking bar may prevent translational and rotational movement of the base of the patient lift (e.g., when the bottom surface is in the lowered position, the docking bar may stabilize the patient lift).

At 508, method 500 may include rotating a body of the patient lift to position a patient over the detachable MR table. The body of the patient lift may couple to the base of the patient lift via a swiveling joint, such as the swiveling joint 224 of FIG. 2. As such, the body of the patient lift may rotate relative to the base of the patient lift. In this way, the position of a patient, such as the patient 240 of FIG. 2, that is supported by the patient lift may be changed without the base of the patient lift moving and instead by rotating the body of the patient lift. The patient may be supported by a sling and a plurality of sling straps, such as the sling 236 and the plurality of sling straps 238 of FIG. 2, which are in turn supported by the body of the patient lift. With the docking bar exerting a force on the supports of the base of the patient lift, and therefore preventing movement of the base, at least a portion of the patient may be positioned directly over at least a portion of the detachable MR table by rotating the body of the patient lift.

At 510, method 500 may include transferring a patient from the patient lift onto the detachable MR table. A pulley, a line and a hanger, which may be non-limiting examples of the pulley 226, the line 228, and the hanger 230 of FIG. 2, respectively, may be used to lower the sling, the plurality of sling straps, and the patient downward onto a top surface of the table. The patient may be moved (e.g., by themselves or an operator) out of the sling, and the body of the patient lift may be rotated to move the sling away from the patient. The pedal on the docking bar may be returned to its original position, which may allow the docking bar to raise away from the base of the patient lift. Further, the patient lift may be moved away from the detachable MR table. In this way, the patient may be transferred from the patient lift onto the detachable MR table.

FIGS. 6-8 show a second embodiment of a detachable MR table that facilitates stabilization of a patient lift, and are described collectively. FIG. 6 illustrates an MR table 602.

The MR table 602 may be configured for use in a medical imaging scanner, such as the MRI apparatus 10 of FIG. 1. Further, at least a portion of the MR table 602 may be configured to be positioned within a bore of a medical imaging scanner. As such, at least a portion of the MR table 602 may be of a suitable shape and size to pass through a bore of a medical imaging scanner, and fit inside of the medical imaging scanner during imaging. While the MR table 602 may be configured for use with the MRI scanner, the MR table 602 may be configured for another suitable medical imaging scanner (e.g., x-ray, CT, PET, SPECT, etc.) without departing from the scope of this disclosure.

In the example illustrated in FIG. 6, one or more surfaces of the MR table 602 may be configured to temporarily couple to a medical imaging scanner (e.g., an MRI scanner). In this way, the MR table 602 may be attached to a medical imaging scanner (e.g., an MRI scanner) for stability during medical imaging, and may be detached and moved away from the medical imaging scanner for patient loading. While the MR table 602 is detached from a medical imaging scanner, the MR table 602 is more susceptible to tipping over due to weight imbalance during patient loading and unloading. Additionally, the reduced stability of the MR table 602 while it is detached from a medical imaging scanner may increase the difficulty of stabilizing a patient lift while transferring a patient onto the MR table 602.

The MR table 602 may be similar to the MR table 300 of FIG. 2, and as such may include a table bed 604, a table midsection 606, and a table base 608. The table midsection 606 may be intermediate the table bed 604 and the table base 608, with the table bed 604 being above the table midsection 606 and the table base 608 being below the table midsection 606, relative to the direction of gravity. The table bed 604 may couple to the table midsection 606, and the table midsection 606 may couple to the table base 608.

The table bed 604 of the MR table 602 may be similar to the table bed 304 of FIG. 2. As such, the table bed 604 may be configured to accommodate a patient during medical imaging. The top surface of the table bed 604 may be flat, relative to the ground. Additionally, at least a portion of the top surface of the table bed 604 may be constructed of a compressible material (e.g., foam, cotton, polyester, etc.). The table bed 604 may have a length in a range of 180-220 cm and a width in a range of 60-92 cm. In some examples, at least one side of the table bed 604 may include rails or guards that may be used to assist a patient on or off of the MR table 602 and/or may provide support for a patient when the MR table 602 is being moved.

The table base 608 of the MR table 602 may provide structural support for the table midsection 606 and the table bed 604 of the MR table 602. In some examples, the table base 608 may have the same length and width as the table bed. As such, the table base 608 may have a length in a range of 180-220 cm and a width in a range of 60-92 cm. Additionally, the table base 608 may have a height in a range of 25-45 cm, from the ground to the highest point of the table base 608.

The table base 608 may include a frame with a plurality of wheels 610, such as the first wheel 612 and the second wheel 702 of FIG. 7 and the third wheel 802 of FIGS. 8A and 8B, that allow the MR table 602 to be moved translationally across a floor. In some examples, the plurality of wheels 610 may include six wheels. The table base 608 may include a plurality of pedals 652 located on the front (e.g., the side most distal to a medical imaging scanner during imaging) of the table base 608. In some examples, the plurality of pedals 652 may actuate the raising and/or lowering of the table bed 604 via a lifting mechanism in the table midsection 606 and the detachment and/or reattachment of the MR table 602 from a medical imaging scanner (e.g., an MRI scanner). Additionally, the table base 608 may include a dock 706 that allows the MR table 602 to attach to a medical imaging scanner. The dock 706 may be located on the back of the table base 608, opposite to the plurality of pedals 652.

The table base 608 may include a housing 614 where the inner volume of the housing 614 may envelope some or all of the table base 608. The housing 614 of the table base 608 may include a cover 704 extending at least partially along one longitudinal side of the MR table 602. As shown in FIG. 7, a first bottom edge 705 of a cutout of the cover 704 may have a higher clearance from the ground on which the MR table 602 sits than a second bottom edge 708 of the rest of cover 704. In some examples, the first bottom edge 705 of the cover 704 may be positioned in a range of 5-30 cm above the floor, and the second bottom edge 708 of the cover 704 may be positioned in a range of 4-10 cm above the floor, when the MR table 602 is raised to a maximum height. In this way, the cover 704 may allow at least a portion of base supports of a patient lift, such as a patient lift 618 of FIG. 6, to fit under the housing 614 of the MR table 602.

The table midsection 606 may include structural elements that at least in part support the table bed 604 against the force of gravity. In some examples, the table midsection 606 may have a shorter length and a narrower width relative to the length and width of the table bed 604, respectively. As such, the table midsection 606 may have a length in a range of 120-185 cm and a width in a range of 40-72 cm. Additionally, the table midsection 606 may include two scissor lift mechanisms, such as a first scissor lift mechanism 804 and a second scissor lift mechanism 806, as shown in FIGS. 8A and 8B. The first scissor lift mechanism 804 and the second scissor lift mechanism 806 may allow the table bed 604 to change height relative to the ground. In some examples, the table bed 604 may have a minimum height of 50 cm and a maximum height of 95 cm.

The first scissor lift mechanism 804 may include a first major arm 808. The first major arm 808 may include a first fixed end 807. In some examples, the first fixed end 807 of the first major arm 808 may couple to a structural member of the MR table 602 that is positioned adjacent to the first wheel 612. In other examples, the first fixed end 807 may couple directly to a portion of the first wheel 612. As illustrated in FIG. 8A, the first wheel 612 may be positioned on the ground on a first side 811 of a vertical axis 810. A second end 809 of the first major arm 808 may couple to a bottom surface of the table bed 604, via a track-like mechanism such as two rails, on a second side 813 of the vertical axis 810.

The first scissor lift mechanism 804 may include a first minor arm 812. Similar to the first major arm 808, a first end 814 of the first minor arm 812 may be positioned on the first side 811 of the vertical axis 810, while a first free end 816 of the first minor arm 812 may be positioned on the second side 813 of the vertical axis 810. The first end 814 of the first minor arm 812 may be on the same side of the vertical axis 810 as the first wheel 612 (e.g., the first side 811), and may couple to a bottom surface of the table bed 604. In some examples, the first end 814 may couple to a bottom surface of the table bed 604 in way that prevents movement of the first end 814. In other examples, the first end 814 may couple to a bottom surface of the table bed 604 via a track-like mechanism, such as two rails, allowing for linear movement of the first end 814.

The first free end 816 of the first minor arm 812 may be positioned on the second side 813 of the vertical axis 810 (e.g., opposite the first wheel 612 and the first end 814) and may be positioned at a height that is lower than the first end 814. Further, the first free end 816 may be positioned vertically higher than the first fixed end 807 of the first major arm 808 when the table bed 604 is in both the raised position (e.g., as shown in FIG. 8B) and the lowered position (e.g., as shown in FIG. 8A). As such, there may be a higher clearance between the first free end 816 of the first minor arm 812 and the ground, than between the first fixed end 807 of the first major arm 808 and the ground. The first free end 816 may be a free end of the first minor arm 812, such that the first free end 816 may not be fixedly coupled (e.g., unable to move) or positioned in a track-like mechanism (e.g., restricted to move in one dimension). As a free end of the first minor arm 812, the first free end 816 may be free to move translationally in two dimensions (e.g., vertically and horizontally).

The first minor arm 812 may couple to the first major arm 808 via a pivot screw, hinge pin, or another suitable coupling mechanism that creates a pivot axis 815. The vertical axis 810 may intersect the pivot axis 815 and may be orthogonal to the pivot axis 815. In some examples, the pivot axis 815 may be positioned at the center of the longitudinal axis of the first major arm 808. When a force is exerted downwards (e.g., toward the ground) or outwards (e.g., toward the end of the MR table 602 where the first wheel 612 is positioned) on the first free end 816 of the first minor arm 812, the first minor arm 812 rotates clockwise around the pivot axis 815. As the first minor arm 812 rotates around the pivot axis 815, the angle A1 between the first major arm 808 and the first minor arm 812 may decrease. As the angle A1 decreases, the first end 814 of the first minor arm 812 and the second end 809 of the first major arm 808 may produce an upward force of the table bed 604, causing the table bed 604 to raise relative to the ground. Additionally, as the table bed 604 raises relative to the ground, the second end 809 of the first major arm 808 may move along the track-like mechanism away from the longitudinal center of the table bed 604 (e.g., toward the first end 814 of the first minor arm 812).

In order to raise the table bed 604 relative to the ground, a force may be exerted on the MR table by a first actuator 822. The first actuator 822 may be a mechanical piston, a hydraulic piston, or another suitable pushing or pulling mechanism. The first actuator 822 may comprise a body 823 and an arm 825, where the arm 825 is configured to move away from (e.g., extend from) the body 823 when the first actuator 822 is activated (e.g., actuated). Additionally, the first actuator 822 may be configured to lock the arm 825 in one or more extended positions to hold the table bed 604 of the MR table 602 in a raised position.

In some examples, as shown in FIGS. 8A and 8B, the body 823 of the first actuator 822 may couple to the first free end 816 of the first minor arm 812 and the arm 825 may couple to a coupling point 824. The coupling point 824 may be positioned on the first major arm 808 between the pivot axis 815 and the second end 809. When activated, the first actuator 822 may exert a force downwards and/or outwards on the first free end 816 of the first minor arm 812 and upwards and/or inwards on the coupling point 824. Due to the forces exerted by the first actuator 822, the first free end 816 may rotate clockwise around the pivot axis 815 and the second end 809 of the first major arm 808 and first end 814 the first minor arm 812 may move upwards. Further, the second end 809 may move along a track toward the vertical axis 810. In turn, the angle A1 of the first scissor lift mechanism 804 may decrease and the table bed 604 may be raised relative to the ground.

In other examples, the body 823 of the first actuator 822 may couple to the first free end 816 of the first minor arm 812 and the arm 825 may couple to the second end 809 of the first major arm 808. When activated, the first actuator 822 may exert a force downwards and/or outwards on the first free end 816 of the first minor arm 812 and upwards and/or inwards on the coupling point 824. Due to the forces exerted by the first actuator 822, the first free end 816 may rotate clockwise around the pivot axis 815 and the second end 809 of the first major arm 808 and first end 814 the first minor arm 812 may move upwards. Further, the second end 809 may move along a track toward the vertical axis 810. In turn, the angle A1 of the first scissor lift mechanism 804 may decrease and the table bed 604 may be raised relative to the ground.

In still other examples, the body 823 of the first actuator 822 may couple to a structural component on the MR table 602 and the arm 825 may couple to a bottom surface of the table bed 604. When activated, the first actuator 822 may exert a force upwards on the table bed 604. Due to the forces exerted by the first actuator 822, the first free end 816 may rotate clockwise around the pivot axis 815 and the second end 809 of the first major arm 808 and first end 814 the first minor arm 812 may move upwards. Further, the second end 809 may move along a track toward the vertical axis 810. In turn, the angle A1 of the first scissor lift mechanism 804 may decrease and the first scissor lift mechanism 804 may provide structural support for the MR table 602 while the table bed 604 is in a raised position.

In some examples, the first actuator 822 may be positioned on the second side 813 of the vertical axis 810. In this way, the first actuator 822 may be positioned further away from a magnet in an MRI scanner when the MR table 602 is being used for an MRI scan than if the first actuator 822 was on positioned on the first side 811 of the vertical axis 810. As such, the amount of force exerted on the first actuator 822 by the magnet in the MRI scanner may be reduced if the first actuator 822 is a magnetic actuator.

In some examples, the first actuator 822 may not couple to the first minor arm 812 on the second side 813 of the vertical axis 810 (e.g., the first free end 816). Instead, in some examples, the body 823 of the first actuator 822 may couple to a structural component on the MR table 602 and the arm 825 may couple to a bottom surface of the table bed 604. In other examples, the body 823 of the first actuator 822 may couple to a portion of the minor arm 812 that is positioned on the first side 811 of the vertical axis 810, and the arm 825 may couple to the coupling point 824. When the first actuator 822 does not couple to the first minor arm 812 on the second side 813 of the vertical axis 810 (e.g., the first free end 816), the portion of the first minor arm 812 that is positioned on the second side 813 of the vertical axis 810 may be eliminated from the MR table 602. However, in such examples, the MR table 602 may still include the portion of the first minor arm 812 that is positioned on the first side 811 of the vertical axis 810. As such, the first clearance gap 818 may be created between the first major arm 808 and the third wheel 802 of the MR table 602.

The second scissor lift mechanism 806 may be similar to the first scissor lift mechanism 804, if the first scissor lift mechanism 804 was mirrored over the vertical axis 810 and positioned at the other longitudinal end of the MR table 602. As such, the second scissor lift mechanism 806 may include a second major arm, a second minor arm, a second free end, a second fixed end, and a second actuator, each similar to the first major arm 808, the first minor arm 812, the first free end 816, the first fixed end 807, and the first actuator 822, respectively.

The movement of the first minor arm 812, including the first free end 816 and the first major arm 808 of the first scissor lift mechanism 804 may exert an upward force on the table bed 604. This force, along with the force exerted on the table bed 604 by the movement of a second minor arm, including a second free end, and a second major arm of the second scissor lift mechanism 806, may cause the table bed 604 to raise relative to the ground. When the MR table 602 is in a raised position, as shown in FIG. 8B, the first free end 816 may be positioned to expose the first clearance gap 818 between the first free end 816 of the first scissor lift mechanism 804 and the third wheel 802. Similarly, a second clearance gap 820 may be created between a second free end of the second scissor lift mechanism 806 and the third wheel 802.

In MR tables that include a single scissor lift mechanism, it is common for the bottommost ends of the scissor lift mechanism (e.g., the first free end 816 of the first minor arm 812) to be positioned in a linear track (e.g., a frame) along the bottom of the MR table. The linear track may guide the movement of the bottommost ends of the scissor lift mechanism as the MR table is lifted and lowered, and constrain the movement of the bottommost ends to a single dimension. Further, the linear track may extend along the entire length of the table base, with no gaps and/or breaks. As such, it may be difficult to create a space of increased clearance between the MR table and the ground, which may prevent supports of a patient lift from being positioned under the MR table.

However, by utilizing two scissor lift mechanisms instead of a single scissor lift mechanism, a linear track that extends along the length of the bottom of the MR table 602 may be excluded. Instead of being constrained within a linear track, the bottommost ends of the first scissor lift mechanism 804 (e.g., the first free end 816) and the second scissor lift mechanism 806 may be free to move in two dimensions (e.g., vertical and horizontal). The outward and upward movement of the first free end 816 as the table bed 604 is lifted may create a space of increased clearance between a bottom portion of the MR table 602 and the ground, such as the first clearance gap 818. Similarly, the movement of a second minor arm of the second scissor lift mechanism 806 may create the second clearance gap 820. The first clearance gap 818 and the second clearance gap 820 may be created in positions that may otherwise be blocked by a linear track if the MR table 602 included only a single scissor lift mechanism. The first clearance gap 818 and the second clearance gap 820 may accommodate supports of a patient lift, allowing the patient lift to be stabilized at the side of the MR table so that a patient may be positioned directly over the MR table 602.

The first clearance gap 818 and the second clearance gap 820 may each accommodate a base support of a patient lift such as the patient lift 618 of FIG. 6. The patient lift 618 may include a base 620 and a body 622, where one longitudinal end of the body 622 couples to a connecting section 624 of the base 620. The body 622 may include a hinge 626, a top end 628, a line 630, and a hanger 632. The hinge 626 may allow a section of the body 622 that is above the hinge 626 to change angle relative to a section of the body 622 that is below the hinge 626. As such, the section of the body 622 that is above the hinge 626 may be lowered closer to the ground to facilitate transfer of a patient, such as a patient 634 of FIG. 6, onto and/or off of the patient lift 618. The line 630 may be a rope, a cable, a chain, or another suitable material, and may couple to the body 622 at the top end 628. The line 630 may support the hanger 632, which in turn may support a plurality of sling straps 636. The plurality of sling straps 636 may wrap around the hanger 632 in order to support a sling 638. The patient 634 may sit in the sling 638 during transfer with the patient lift 618.

As shown in FIG. 6, the body 622 of the patient lift 618 may couple to the base 620 at the highest point of the connecting section 624 (e.g., relative to the ground). Along with the connecting section 624, the base 620 may include a first support 640 and a second support 642 each of which may couple to the connecting section 624. As illustrated in FIG. 7, one longitudinal end of the first support 640 may couple to a first arm 644 of the connecting section 624, and one longitudinal end of the second support 642 may couple to a second arm 646 of the connecting section 624. The base 620 may include a plurality of wheels 648, such as a first wheel 650, some of which may couple to a bottom surface of the connecting section 624 and others to a bottom surface of the first support 640 or a bottom surface of the second support 642. The plurality of wheels 648 may allow the patient lift 618 to move translationally across the floor.

While supporting the patient 634, the patient lift 618 may be positioned such that at least a portion of the first support 640 and at least a portion of the second support 642 of the base 620 are under the MR table 602, as shown in FIGS. 6 and 7. In this position, the first support 640 may be positioned in the first clearance gap 818 and the second support 642 may be positioned in the second clearance gap 820. As such, at least a portion of the sling 638 may be positioned directly over the MR table 602 and may increase the case of transferring the patient 634 from the patient lift 618 onto the table bed 604 relative to if none of, or a smaller portion of, the sling 638 was positioned directly over the MR table 602.

FIG. 9 is a flowchart illustrating a method 900 for transferring a patient from a patient lift to a detachable MR table. The patient lift may be a non-limiting example of the patient lift 618 of FIG. 6. Similarly, the detachable MR table may be a non-limiting example of the MR table 602 of FIG. 6. Method 900 may be executed by an operator, such as a nurse, technologist, staff member, or other suitable person.

At 902, method 900 may include raising a detachable MR table to a target position to create clearance gaps. In some examples, the target position may be a highest possible position the table may be placed into. In other examples, the target position may be a position at which sufficient clearance gaps are created. The detachable MR table may be a non-limiting example of the MR table 602 of FIGS. 6-8B, and may therefore have a cover on one longitudinal side of a table base, such as the cover 704 of FIGS. 6 and 7. The table bed of the detachable MR table may be lifted to, and held in, a raised position such as the position shown in FIG. 8B. The table bed may be raised by two scissor lift mechanisms, such as the first scissor lift mechanism 804 and the second scissor lift mechanism 806 of FIGS. 8A and 8B. In some examples, a force may be exerted on a minor arm of each of the two scissor lifts by an actuator, such as a mechanical piston, a hydraulic piston, a pulley, or another suitable pushing and/or pulling mechanism, in order to raise the table bed. In other examples, a force may be exerted on a bottom surface of the table bed by the actuator to raise the table bed.

Both scissor lift mechanisms may close (e.g., a bottom angle between the major and minor arm of each scissor lift mechanism may decrease) due to the force exerted on the table or each scissor lift mechanism. As such, each of the minor arms and major arms may rotate around a pivot axis to an orientation that is closer to perpendicular with the ground. When the table bed is in a raised position, and each of the scissor lift mechanisms are closed, there may be two clearance gaps, such as the first clearance gap 818 and the second clearance gap 820 of FIG. 8B, between free ends of the minor arms of the scissor lift mechanisms and the wheels of the detachable MR table.

At 904, method 900 may include rolling a base of a patient lift under the detachable MR table with the supports of the base of the patient lift positioned in the clearance gaps. The lower side panel, such as the cover 704 of FIG. 7, may allow at least a portion of the base of the patient lift to fit underneath the detachable MR table. As such, the patient lift may be oriented so that supports of the base of the patient lift are perpendicular to the side of the detachable MR table that includes the lower side panel. Additionally, when the detachable MR table is in a raised positon, the supports of the base of the patient lift, such as the first support 640 and the second support 642 of FIG. 6, may fit into two clearance gaps under the detachable MR table, such as the first clearance gap 818 and the second clearance gap 820 of FIG. 8B. In this way, a larger portion of the base of the patient lift may fit underneath the detachable MR table than if the detachable MR table was in a lowered position (e.g., if each of the scissor lift mechanisms of the detachable MR table were in an open position). With the supports of the base of the patient lift positioned underneath the detachable MR table, at least a portion of a patient being supported by the patient lift may be positioned directly above at least a portion of the detachable MR table.

At 906, method 900 may include transferring a patient from the patient lift onto the detachable MR table. The patient may be supported by a sling and sling straps, which are in turn supported by a body of the patient lift. In some examples, a top section of the patient lift may be lowered (e.g., angled downward) to lower the sling and/or the patient onto a top surface of the table bed. The patient may be moved (e.g., by themselves or an operator) out of the sling, and the patient lift may be moved away from the detachable MR table. In this way, the patient may be transferred from the patient lift onto the detachable MR table.

Thus, the MR table 300 and the MR table 602 described herein may facilitate stabilization of a patient lift. The MR table 300 may include a docking bar coupled to one longitudinal side of the table base via a hinge-like mechanism. The docking bar may rotate from a first position, which is parallel to the table base, to a second position, which is perpendicular to the table base. An operator may actuate the lowering of the docking bar onto the supports of a patient lift in order to apply a stabilizing downward force onto the base of the patient lift. The MR table 602 may include two scissor lift mechanisms within the table midsection which may allow the table bed to raise relative to the table base. When the scissor lift mechanisms are moved into a more closed state, and the table bed is in a raised position, clearance gaps may be formed between the scissor lift mechanisms and the wheels of the MR table. The clearance gaps may accommodate the supports of a patient lift, allowing the supports to be positioned underneath the MR table. The weight of the MR table may therefore hold the supports in place, and stabilize the entire patient lift.

In this way, the docking bar of the MR table 300 and the two scissor lift mechanisms of the MR table 602 described herein may increase the stabilization of a patient lift when transferring a patient from the patient lift onto the MR table. Increased stabilization of the patient lift may allow for an easier patient transfer, decreasing the amount of time needed between MRI scans. Additionally, the docking bar and two scissor lift mechanisms may prevent a patient lift from tipping over during patient transfer. In this way, the safety of both the patient and the operator may be increased.

The disclosure also provides support for a patient table, comprising: a bed coupled to a base via a midsection, and a docking bar coupled to the base, the docking bar movable between a first position where a first longitudinal axis of the docking bar is parallel to a second longitudinal axis of the base and a second position where the first longitudinal axis is perpendicular to the second longitudinal axis, the docking bar including a releasable bottom surface configured to be brought into contact with a base support of a patient lift. In a first example of the patient table, the midsection is configured to house a lift mechanism configured to raise and lower the bed relative to the base. In a second example of the patient table, optionally including the first example, the base includes a frame coupled to a plurality of wheels. In a third example of the patient table, optionally including one or both of the first and second examples, the docking bar is coupled to the frame via a hinge and is configured to move from the first position to the second position via rotation around the hinge. In a fourth example of the patient table, optionally including one or more or each of the first through third examples, the docking bar includes a pedal that when actuated causes the bottom surface to be released and thereby move into contact with the base support of the patient lift. In a fifth example of the patient table, optionally including one or more or each of the first through fourth examples, the bottom surface of the docking bar, when released, is configured to move downward by an amount in a range of 5-15 cm. In a sixth example of the patient table, optionally including one or more or each of the first through fifth examples, the patient table further comprises: a dock configured to couple the patient table to a medical imaging scanner. In a seventh example of the patient table, optionally including one or more or each of the first through sixth examples, the medical imaging scanner is a magnetic resonance imaging scanner. In an eighth example of the patient table, optionally including one or more or each of the first through seventh examples, the docking bar is comprised of non-ferrous material.

The disclosure also provides support for a docking bar for a patient table, comprising: a body including a connecting end configured to be pivotably mounted on the patient table via a hinge mechanism, and a lift stabilizer at least partially housed within the body, the lift stabilizer including a releasable bottom surface configured to be brought into contact with a base support of a patient lift. In a first example of the docking bar, the lift stabilizer further includes an actuator configured to release the bottom surface from a retracted position to a deployed position, wherein the bottom surface is configured to contact the base support of the patient lift when in the deployed position. In a second example of the docking bar, optionally including the first example, the system further comprises: a pedal coupled to the actuator and configured to cause the actuator to release the bottom surface or retract the bottom surface. In a third example of the docking bar, optionally including one or both of the first and second examples, the bottom surface, when released, is configured to move downward by an amount in a range of 5-15 cm. In a fourth example of the docking bar, optionally including one or more or each of the first through third examples, the body and the lift stabilizer are each comprised of non-ferrous material.

The disclosure also provides support for a patient table configured to stabilize a patient lift, comprising: a bed coupled to a base via a midsection, a first scissor lift mechanism, and a second scissor lift mechanism, each of the first scissor lift mechanism and the second scissor lift mechanism housed in the midsection and coupled to the base and to the bed and configured to raise the bed from a lowered position to a raised position, wherein at least in the raised position, a first clearance gap and a second clearance gap is exposed within the base between the first scissor lift mechanism and the second scissor lift mechanism. In a first example of the patient table, the first scissor lift mechanism includes a first free end and the second scissor lift mechanism includes a second free end, and wherein in the raised position, each of the first free end and the second free end is moved to expose the first clearance gap and the second clearance gap, and further comprising a frame and a plurality of wheels coupled to the frame, and wherein: the first scissor lift mechanism includes a first major arm and a first minor arm, a first fixed end of the first major arm coupled to the frame and/or one wheel of the plurality of wheels, wherein the first free end is an end of the first minor arm and in both the raised position and the lowered position, the first free end is positioned vertically higher than the first fixed end, and the second scissor lift mechanism includes a second major arm and a second minor arm, a second fixed end of the second major arm coupled to the frame and/or another wheel of the plurality of wheels, wherein the second free end is an end of the second minor arm and in both the raised position and the lowered position, the second free end is positioned vertically higher than the second fixed end. In a second example of the patient table, optionally including the first example, the first scissor lift mechanism includes a first actuator coupled to the first free end and the first major arm and the second scissor lift mechanism includes a second actuator coupled to the second free end and the second major arm. In a third example of the patient table, optionally including one or both of the first and second examples, the first free end and the second free end are configured to move both vertically and horizontally, and wherein each of the first free end and the second free end are not coupled to or housed within a track or rails. In a fourth example of the patient table, optionally including one or more or each of the first through third examples, the system further comprises: a cover extending at least partially along the base, wherein the cover includes a cutout at the first clearance gap and the second clearance gap, and wherein a first bottom edge of the cutout has a higher clearance relative to a ground on which the patient table sits than a second bottom edge of a remaining portion of the cover. In a fifth example of the patient table, optionally including one or more or each of the first through fourth examples, the system further comprises: a dock configured to couple the patient table to a magnetic resonance imaging scanner.

As used herein, the term “approximately” is construed to mean plus or minus five percent of the range unless otherwise specified.

The following claims particularly point out certain combinations and sub-combinations regarded as novel and non-obvious. These claims may refer to “an” element or “a first” element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A patient table, comprising:

a bed coupled to a base via a midsection; and a docking bar coupled to the base, the docking bar movable between a first position where a first longitudinal axis of the docking bar is parallel to a second longitudinal axis of the base and a second position where the first longitudinal axis is perpendicular to the second longitudinal axis, the docking bar including a releasable bottom surface configured to be brought into contact with a base support of a patient lift.

2. The patient table of claim 1, wherein the midsection is configured to house a lift mechanism configured to raise and lower the bed relative to the base.

3. The patient table of claim 2, wherein the base includes a frame coupled to a plurality of wheels.

4. The patient table of claim 3, wherein the docking bar is coupled to the frame via a hinge and is configured to move from the first position to the second position via rotation around the hinge.

5. The patient table of claim 4, wherein the docking bar includes a pedal that when actuated causes the bottom surface to be released and thereby move into contact with the base support of the patient lift.

6. The patient table of claim 5, wherein the bottom surface of the docking bar, when released, is configured to move downward by an amount in a range of 5-15 cm.

7. The patient table of claim 1, further comprising a dock configured to couple the patient table to a medical imaging scanner.

8. The patient table of claim 7, wherein the medical imaging scanner is a magnetic resonance imaging scanner.

9. The patient table of claim 8, wherein the docking bar is comprised of non-ferrous material.

10. A docking bar for a patient table, comprising:

a body including a connecting end configured to be pivotably mounted on the patient table via a hinge mechanism; and a lift stabilizer at least partially housed within the body, the lift stabilizer including a releasable bottom surface configured to be brought into contact with a base support of a patient lift.

11. The docking bar of claim 10, wherein the lift stabilizer further includes an actuator configured to release the bottom surface from a retracted position to a deployed position, wherein the bottom surface is configured to contact the base support of the patient lift when in the deployed position.

12. The docking bar of claim 11, further comprising a pedal coupled to the actuator and configured to cause the actuator to release the bottom surface or retract the bottom surface.

13. The docking bar of claim 11, wherein the bottom surface, when released, is configured to move downward by an amount in a range of 5-15 cm.

14. The docking bar of claim 10, wherein the body and the lift stabilizer are each comprised of non-ferrous material.

* * * * *